United States Patent
Horger et al.

(10) Patent No.: US 9,704,053 B2
(45) Date of Patent: Jul. 11, 2017

(54) METHOD AND MAGNETIC RESONANCE APPARATUS FOR PLANNING A SPECTROSCOPY MEASUREMENT

(71) Applicant: Siemens Aktiengesellschaft, Munich (DE)

(72) Inventors: Wilhelm Horger, Schwaig (DE); Miriam Keil, Erlangen-Dechsendorf (DE)

(73) Assignee: Siemens Aktiengesellschaft, Munich (DE)

(*) Notice: Subject to any disclaimer, the term of this patent is extended or adjusted under 35 U.S.C. 154(b) by 5 days.

(21) Appl. No.: 14/854,475

(22) Filed: Sep. 15, 2015

(65) Prior Publication Data

US 2016/0078616 A1    Mar. 17, 2016

(30) Foreign Application Priority Data

Sep. 16, 2014  (DE) .................. 10 2014 218 560

(51) Int. Cl.

| | | |
|---|---|---|
| *G06K 9/46* | (2006.01) | |
| *A61B 5/055* | (2006.01) | |
| *G01R 33/54* | (2006.01) | |
| *G01R 33/483* | (2006.01) | |
| *G01R 33/46* | (2006.01) | |

(52) U.S. Cl.

CPC .............. *G06K 9/46* (2013.01); *A61B 5/055* (2013.01); *G01R 33/543* (2013.01); *G01R 33/46* (2013.01); *G01R 33/483* (2013.01)

(58) Field of Classification Search

CPC ........ G06K 9/46; G01R 33/543; G01R 33/46; G01R 33/483; G01R 33/56563; G01R 33/56572; G01R 33/5659; G01R 33/565; A61B 5/055; A61B 2018/00351; G06T 7/0012; G06T 2207/30196; G06T 2207/30004; G06T 2207/30048; G06T 2207/10088

See application file for complete search history.

(56) References Cited

U.S. PATENT DOCUMENTS

| | | | |
|---|---|---|---|
| 7,782,054 B2 | 8/2010 | Werthner | |
| 7,902,824 B2 | 3/2011 | Werthner | |
| 2007/0223800 A1 | 9/2007 | Guehring | |
| 2008/0036458 A1* | 2/2008 | Tatebayashi | G01R 33/483 324/307 |
| 2008/0267509 A1 | 10/2008 | Springorum et al. | |
| 2009/0174405 A1* | 7/2009 | Kassai | G01R 33/56572 324/309 |

(Continued)

*Primary Examiner* — Sumati Lefkowitz
*Assistant Examiner* — Carol Wang
(74) *Attorney, Agent, or Firm* — Schiff Hardin LLP

(57) ABSTRACT

In a method for planning a spectroscopy measurement of an examination object by operation of a magnetic resonance apparatus, an image data record is selected that includes at least two images of a magnetic resonance measurement of the examination object, an isometric and/or isogonal region is determined in a first image of the at least two images, a region of interest is selected according to the isometric and/or isogonal region determined on the first image, and the first image is displayed, at least one further, second image of the image data record is displayed according to the selected region of interest, and the spectroscopy measurement is planned according to the displayed images.

9 Claims, 1 Drawing Sheet

(56) References Cited

U.S. PATENT DOCUMENTS

2009/0224761 A1* 9/2009 Umeda ................ G01R 33/485
324/312
2010/0158338 A1 6/2010 Harder et al.
2012/0268118 A1 10/2012 Fenchel et al.

* cited by examiner

METHOD AND MAGNETIC RESONANCE APPARATUS FOR PLANNING A SPECTROSCOPY MEASUREMENT

BACKGROUND OF THE INVENTION

Field of the Invention

The present invention concerns a method for planning a spectroscopy measurement of an examination object by operation of a magnetic resonance apparatus, as well as a magnetic resonance apparatus and a non-transitory, computer-readable storage medium encoded with programming instructions to perform such a method.

Description of the Prior Art

Magnetic resonance tomography (MRT) is an imaging modality that enables the high-resolution generation of sectional views of living organisms, such as humans. The patient is supported in a homogeneous magnetic field $B_0$. This basic magnetic field in the FOV (field of view) is modified with gradient coils such that a body slice is selected and a spatial encoding of the generated magnetic resonance (MR) signals takes place. In the subsequent reconstruction of MR signals, for instance by Fourier transformation, an image of the selected slice is produced, which is used for medical diagnostics. The generation and detection of MR signals takes place using a radio frequency system, that includes a transmit antenna, which radiates radio frequency (RF) excitation pulses into the patient, and a reception antenna, which detects the emitted RF resonance signals and forwards the detected signals for image reconstruction. By selecting a suitable pulse sequence, such as a spin echo sequence or a gradient echo sequence, and the sequence parameters associated therewith, the contrast of the MR images can be varied diversely depending on the diagnostic task to be performed. MRT maps body structures and accordingly represents a structural imaging method.

A method based on nuclear spin resonance is referred to as magnetic resonance spectroscopy (MRS), with which biochemical observations can be performed in a spatially resolved manner in a volume element. Different chemical substances can thus be identified and quantified in the living tissue by their chemical shift. Within the scope of magnetic resonance spectroscopy, a specific volume, which has previously been positioned using overview images, can be measured in a tissue.

The planning of spectroscopy protocols on a magnetic resonance apparatus is conventionally subject to several technical limitations. Therefore, these must be planned with the use of non-distortion-corrected images, and the bed position of an examination bed being used within the magnetic resonance device must be known. These limitations may result in restrictions in the resulting image quality and require a high degree of knowledge relating to the underlying examination process.

SUMMARY OF THE INVENTION

An object of the present invention is to provide a method that facilitates planning of such a spectroscopy measurement, and provides for increased user convenience.

This object is achieved in accordance with the invention by a method for planning a spectroscopy measurement of an examination object by operation of a magnetic resonance that includes the following steps. An image data record is selected that includes at least two images of a magnetic resonance measurement of the examination object. An isometric and/or isogonal region in a first image of the at least two images is determined. A region of interest is selected according to the isometric and/or isogonal region determined in the first image, and the first image is displayed with this region of interest. At least one further, second image of the image data record is displayed according to the selected region of interest. The spectroscopy measurement is planned according to the displayed images.

An image data record that includes at least two images of a magnetic resonance measurement of an examination object represents the starting point of the planning.

An isometric and/or isogonal region is then determined in a first image of the at least two images. Here, an isometric and/or isogonal region is understood to be a region in which effects of distortion correction are kept to a minimum, i.e. a region which is subject to fewer distortions depending on the recording than for instance a region on edge positions of an image. This determination preferably takes place automatically. This ensures that the spectroscopy measurement is not planned too far outside of an isocenter, since the spatial information there could be incorrect on account of field distortions and the field homogeneity may not be optimal. This may in turn have negative effects on the image or spectra quality.

Subsequently, a region of interest is selected according to the isometric and/or isogonal region determined on the first image and said first image is displayed. Here, a region of interest is understood to mean that region in which the spectroscopy measurement is to be performed. Advantageously only one region of interest which lies within the previously determined isometric and/or isogonal region can be selected.

The display of at least one further, second image of the image data record depending on the selected region of interest takes place in order to obtain a control level which is additionally required for a spectroscopy measurement. Here, a control level is understood to mean an image which was measured in another orientation level. An orientation level is understood to mean for instance, but not exclusively, a transverse plane, a sagittal plane or a coronal plane. The control level preferably lies in an image plane at right angles to the first image.

The planning of the spectroscopy measurement can take place using the images displayed in this way and a specific volume, which is now present positioned on overview images, can be measured in a tissue. Spectroscopy measurements can in this way integrate into any conceivable operational process. Already measured planning images no longer need to be adjusted manually.

In an embodiment, the method further includes a removal of a distortion correction on the first image. This removal preferably takes place automatically after selecting the region of interest according to the isometric and/or isogonal region determined on the first image.

In a further embodiment, the method includes removal of a distortion correction of the further displayed images. The removal of this distortion correction preferably takes place prior to displaying the at least one further, second image of the image data record according to the selected region of interest.

In a preferred embodiment, the region of interest comprises a couch position. This can thus ensure that in the further course of the method, planning images can be selected which were recorded at the same couch position, which increases the accuracy of the spectroscopy measurement.

In an advantageous embodiment, the display of the at least one further image takes place according to the couch position, i.e. that images are preferably displayed, which were measured at the same couch position. This also serves to increase the accuracy of the spectroscopy measurement.

In a further embodiment, the display of the at least one further, second image includes a calculation of at least one additional image based on the first selected image. This can ensure that at least one second image can be used for the spectroscopy planning even if there is no further image present, which was measured at the couch position of the first image. At least one further orientation level thus also exists for this case.

In a preferred embodiment, the selection of the region of interest includes an active confirmation and/or selection. Here, confirmation and/or selection is understood to mean a manual control by a user who verifies the region of interest once again. This serves to prevent an inadvertent selection of an unwanted region of interest.

Within the scope of the present invention, a magnetic resonance device is also provided to determine a type of reconstruction of image data of a magnetic resonance measurement of an examination object.

The magnetic resonance apparatus includes a planning computer and a processing computer configured to perform selection of an image data record that includes at least two images of a magnetic resonance measurement of the examination object by the processing computer, determination of an isometric and/or isogonal region on a first image of the at least two images by the processing computer, selection of a region of interest according to the isometric and/or isogonal region determined on the first image and displaying the first image by the processing computer, display of at least one further, second image of the image data record according to the selected region of interest by means of the processing computer, and planning of the spectroscopy measurement according to the displayed images by the planning computer.

Furthermore, the present invention concerns a storage medium that can be loaded into a memory unit of a programmable controller or a computer of a magnetic resonance apparatus. All or some of the above-described embodiments of the inventive method can be executed by programming instructions encoded in the storage medium being executed by the controller or control computer of the magnetic resonance apparatus. The programming instructions may possibly require program means, e.g. libraries and auxiliary functions, in order to realize the corresponding embodiments of the method. The software may be a source code which must still be compiled and linked or which only has to be interpreted, or an executable software code, which for execution purposes only has to be loaded into the corresponding computing unit.

The electronically readable storage medium can be, e.g. a DVD, a magnetic tape or a USB stick, on which the electronically readable control information, in particular software, is stored.

The advantages of the inventive magnetic resonance apparatus and the inventive electronically readable storage medium essentially correspond to the advantages of the inventive method, which are explained above in detail. Features, advantages or alternative embodiments mentioned herein are likewise applicable to the other aspects of the invention. The functional features of the method are embodied as suitable representational modules, in particular by hardware modules.

DESCRIPTION OF THE PREFERRED EMBODIMENTS

Figure 1:
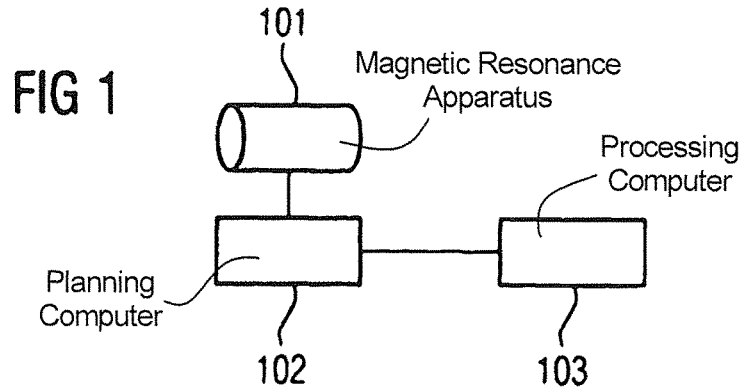
FIG. 1 shows an inventive magnetic resonance apparatus.

FIG. 1 shows an inventive magnetic resonance apparatus 101 that includes a scanner as schematically illustrated. The magnetic resonance apparatus 101 has a planning computer 102 and a processing computer 103 and is designed to perform a method for planning a spectroscopy measurement of an examination object.

The magnetic resonance apparatus 101 is embodied here as a pure magnetic resonance device 101. Alternatively the magnetic resonance device 101 can be a combined magnetic resonance positron emission tomography device.

Figure 2:
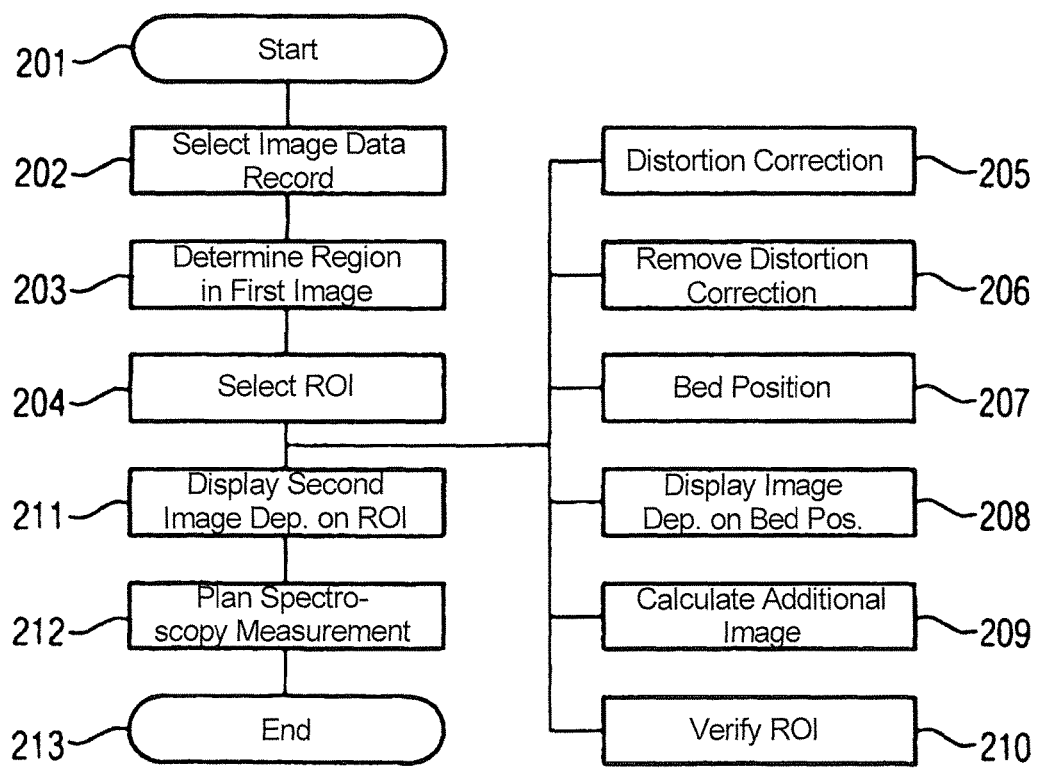
FIG. 2 is a flowchart of an inventive method.

FIG. 2 is a flowchart of a method according to the invention. The method comprises the method steps 201 to 213, wherein, when describing the method steps 201 to 213, description parts including the corresponding reference characters introduced in conjunction with those in FIG. 1 are also used.

A first method step 201 designates the start of a method for planning a spectroscopy measurement of an examination object by operation of the magnetic resonance apparatus 101.

In method step 202, an image data record is selected, comprising at least two images of a magnetic resonance measurement of the examination object. This represents the starting point of the planning.

Method step 203 comprises the determination of an isometric and/or isogonal region on a first image of the at least two images. Here, an isometric and/or isogonal region is understood to be a region in which effects of distortion correction are kept to a minimum, i.e. a region which is subject to fewer distortions depending on the recording than for instance a region at boundary positions of an image. This determination preferably takes place automatically.

During method step 204, a region of interest (ROI) is selected according to the isometric and/or isogonal region determined on the first image and the first image is displayed. Here, a region of interest is understood to mean that region in which the spectroscopy measurement is to be performed. Advantageously only one region of interest which lies within the previously determined isometric and/or isogonal region can be selected.

In a method step 205, an optional method step, a distortion correction on the first image is removed. This removal preferably takes place automatically after selecting the region of interest according to the isometric and/or isogonal region determined on the first image.

Method step 206, likewise an optional method step, includes a removal of a distortion correction of the further displayed images. The removal of this distortion correction preferably takes place prior to displaying the at least one further, second image of the image data record according to the selected region of interest.

In the optional method step 207, the region of interest includes a bed position and it can be ensured that during the further course of the method, planning images can be selected which were recorded at the same bed position.

In the optional method step 208, the at least one further image is displayed according to the bed position, i.e. images are preferably displayed, which were measured at the same couch position.

In method step 209, likewise an optional method step, the display of the at least one further, second image includes a calculation of at least one addition image based on the first selected image. This can ensure that at least one second image can be used for the spectroscopy planning even if there is no further image present, which was measured at the couch position of the first image and at least one further orientation level thus also exists for this case.

In an optional method step 210, the selection of the region of interest includes an active confirmation and/or selection. Here, confirmation and/or selection is understood to mean a manual control by a user who verifies the region of interest once again.

When executing the inventive method, the method steps 205 to 210 can be used alternatively or also combined with one another.

During a method step 211, at least one further, second image of the image data record is displayed according to the selected region of interest in order to obtain a control level which is additionally required for a spectroscopy measurement. Here, a control level is understood to mean an image which was measured in another orientation level. An orientation level is understood to mean for instance, but not exclusively, a transversal plane, a sagittal plane or a coronal plane.

In method step 212, the planning of the spectroscopy measurement takes place according to the displayed images and a specific volume, which is now present positioned on overview images, can now be measured in a tissue.

A last method step 213 designates the end of a method for planning a spectroscopy measurement of an examination object by means of a magnetic resonance device 101.

In summary, the invention concerns a method for planning a spectroscopy measurement of an examination object by operation of a magnetic resonance apparatus and includes the steps of selecting an image data record comprising at least two images of a magnetic resonance measurement of the examination object, determining an isometric and/or isogonal region on a first image of the at least two images, selecting a region of interest according to the isometric and/or isogonal region determined on the first image and displaying the first image, displaying at least one further, second image of the image data record according to the selected region of interest and planning the spectroscopy measurement according to the displayed images.

In an embodiment, the method further includes a removal of a distortion correction and the region of interest includes a bed position.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method for planning a spectroscopy measurement of examination object by operation of a magnetic resonance apparatus, comprising:
   selecting an image data record comprising at least two images of a magnetic resonance measurement of the examination object;
   determining an isometric and/or isogonal region on a first image of the at least two images;
   selecting a region of interest according to the isometric and/or isogonal region determined on the first image and displaying the first image;
   displaying at least one further, second image of the image data record according to the selected region of interest; and
   planning the spectroscopy measurement according to the displayed images.

2. The method as claimed in claim 1, further comprising removing a distortion correction on the first image.

3. The method as claimed in claim 1, further comprising removing a distortion correction of the further displayed images.

4. The method as claimed in claim 1, comprising selecting the region of interest to include a bed position in the magnetic resonance apparatus.

5. The method as claimed in claim 4, wherein the at least one further, second image is displayed according to the bed position.

6. The method as claimed in claim 1, comprising displaying the at least one further, second image by calculating at least one additional image based on the first image.

7. The method as claimed in claim 1, comprising selecting the region of interest followed by an active confirmation and/or selection.

8. A magnetic resonance apparatus comprising:
   a magnetic resonance scanner configured to execute a magnetic resonance spectroscopy measurement;
   a processor configured to select an image data record comprising at least two images of a magnetic resonance measurement of the examination object;
   said processor being configured to determine an isometric and/or isogonal region on a first image of the at least two images;
   a display in communication with said processor;
   said processor being configured to select a region of interest according to the isometric and/or isogonal region determined on the first image and display the first image at said display;
   said processor being configured to display at least one further, second image of the image data record at said display according to the selected region of interest; and
   a planning computer configured to plan the spectroscopy measurement according to the displayed images and to emit a spectroscopy measurement plan in electronic form to said scanner.

9. A non-transitory, computer-readable data storage medium encoded with programming instructions, said storage medium being distributively loaded into a processing computer and a planning computer of a magnetic resonance apparatus, and said programming instructions causing:
   said processing computer to select an image data record comprising at least two images of a magnetic resonance measurement of an examination object;
   said processing computer to determine an isometric and/or isogonal region on a first image of the at least two images;
   said processing computer to select a region of interest according to the isometric and/or isogonal region determined on the first image and displaying the first image;
   said processing computer to display at least one further, second image of the image data record according to the selected region of interest; and
   said planning computer to plan the spectroscopy measurement according to the displayed images.

* * * * *